United States Patent

Klopping

[11] 3,984,568
[45] Oct. 5, 1976

[54] FUNGICIDAL CYCLOPROPYL SUBSTITUTED 2-CYANOACETAMIDE DERIVATIVES

[75] Inventor: Hein Louis Klopping, Wilmington, Del.

[73] Assignee: E. I. Du Pont de Nemours and Company, Wilmington, Del.

[22] Filed: Sept. 11, 1975

[21] Appl. No.: 612,548

[52] U.S. Cl................................ 424/304; 260/464; 424/DIG. 8
[51] Int. Cl.².................... A01N 9/06; A01N 9/20; C07C 119/00
[58] Field of Search...................... 260/464; 424/304

[56] References Cited
UNITED STATES PATENTS 2,313,498  3/1943  Allen et al. ......................... 260/464
3,625,987  12/1971  Hubele ............................. 260/464

OTHER PUBLICATIONS

Chemical Abstracts, vol. 70, (1969), p. 57388g.

*Primary Examiner*—V. D. Turner

[57] ABSTRACT

Compounds of the formula

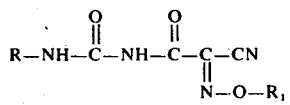

wherein
R is cyclopropyl or cyclopropylmethyl and $R_1$ is alkyl of 1 or 2 carbon atoms are effective plant disease control agents.

6 Claims, No Drawings

FUNGICIDAL CYCLOPROPYL SUBSTITUTED 2-CYANOACETAMIDE DERIVATIVES

BACKGROUND OF THE INVENTION

This invention relates to fungicidal compounds and their use in controlling plant diseases.

There are many commercial formulations available for control of fungus diseases of plants. However, new fungicides are needed to provide better control of particular plant diseases, and control strains of fungi which are not susceptible to commercially available products. The compounds of this invention are particularly effective against certain phycomycetes, for example late blight of tomato and potato and downy mildew of grapes. Unlike many commercially available products, the compounds of this invention not only prevent the attack of a fungus against plants, they also can eradicate the fungus after the plant has become infected.

SUMMARY OF THE INVENTION

Compounds of the formula

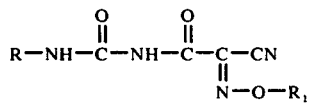

wherein

R is cyclopropyl or cyclpropylmethyl and $R_1$ is alkyl of 1 or 2 carbon atoms are useful in inhibiting fungus diseases in plants. Disease control includes the prevention, inhibition and/or eradication of a plant disease.

The compounds of this invention may be applied to plants to prevent infection of the plants by fungi. The compounds are not only preventive in their action but are also systemic and curative. That is, the compounds are absorbed by plants and move within the plants. Thus, they can eradicate a fungus which has already infected the plant. Because the compounds are systemic, they may be applied not only to the infected or threatened plant parts but also to uninfected parts or to the soil in which the plant grows. All of these sites of application are included within the term "applying to the plants".

The fact that the compounds of this invention are systemic makes them particularly well suited for combination with conventional preventive fungicides. Thus, the compositions of this invention consist essentially of a fungicidally effective amount of a compound of this invention but another fungicidally active ingredient and conventional formulating agents can also be included.

The compounds of this invention wherein $R_1$ is methyl, 2-cyano-N-cyclopropylcarbamoyl-2-methoxyiminoacetamide and 2-cyano-N-cyclopropylmethylcarbamoyl-2-methoxyiminoacetamide are preferred for their fungicidal activity.

DETAILED DESCRIPTION OF THE INVENTION

The novel compounds of this invention can be conveniently prepared by two different routes.

In the first of these routes, 2-cyano-2-methoxyiminoacetamide (O. Diels and E. Borgwardt, Ber. 54, 1342 (1921) or a corresponding higher alkoxyimino homolog of this starting material is converted to the anion of the amide, for example, by means of sodium methoxide or sodium hydride in a suitable inert solvent such as tetrahydrofuran. This anion is reacted with an isocyanate R-NCO, where R is 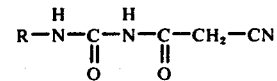. This reaction affords the anion of the product; the product is obtained by acidification in aqueous medium.

In the second of these two routes, an amine $R-NH_2$ is converted to the corresponding urea by means of a cyanate such as potassium cyanate, and the urea is reacted with cyanoacetic acid and acetic anhydride to give a cyanoacetyl urea of the general formula $$R-N(H)-C(=O)-N(H)-C(=O)-CH_2-CN$$

This intermediate is then converted to the oxime by means of sodium nitrite or a suitable alkyl nitrite by methods known in the art. The hydroxyimino group is alkylated by known methods, for example by conversion to the sodium salt by means of sodium methoxide using DMF as the solvent and adding the appropriate alkylating agent. Suitable alkylating agents include alkyl iodides and bromides. Dialkyl sulfates may also be used.

The compounds of this invention are useful as plant disease control agents. Most have qualities of systemic and curative activity when applied to soil, to propagation pieces, to stems, or to foliage. Combinations with other fungicides, especially those with strong residual properties, provide particularly exceptional disease control. The systemic and curative effects of the disease-control agents of this invention make a unique contribution to such combinations. For this reason, compositions containing another fungicide along with a compound of this case are often preferred. The systemic property of the compounds of this case is strikingly evident in the control of potato and tomato late blight disease on the foliage when treatments with the compounds are applied solely to the root system. Additional evidence comes from the curative action against established infections by the causal agent of late blight disease or downy mildew of grapes. The disease can be arrested even when treatments are delayed hours after plants have been infected.

Of the fungi causing diseases on agricultural crops, those classed as Phycomycetes are among the most virulent. The disorders caused by this group of fungi include late blight of tomatoes and potatoes, as well as downy mildew of grapes, cole crops, legumes, and cucurbits. Diseases caused by Phycomycetes are especially susceptible to control by the compounds of this invention.

The compounds of this invention provide protection from damage caused by certain fungi when applied to the proper locus by the methods described hereinafter and at a sufficient rate to exert the desired effect. They are suited for the protection of living plants by applying the compounds of this invention to the soil in which they are growing or in which they may subsequently be seeded or planted, to seeds, tubers, bulbs, or other plant reproductive parts prior to planting, as well as to foliage, stems and/or fruit. Soil applications are made from dusts, granules, pellets, solutions, emulsions, or slurries.

Preferred rates for application of the compounds of this invention to soil in which plants are or will be growing range from 0.5 to 500 p.p.m. by weight of the soil in which the roots are or will be growing. More preferred use rates are in the range of 1 to 200 parts per million. The most preferred rates are in the range of 5 to 100 ppm. Preferred rates for application to seeds, tubers, bulbs, or other plant reproductive parts range from 0.5 to 100 g of active compound of this invention per kilo of planting material treated. More preferred rates are in the range of 1 to 75 g of active compound per kilo. The most preferred rates are in the range of 2 to 50 g per kilo. Applications of this type are made from dusts, slurries, emulsions, or solutions.

Preferred rates of application for the compounds of this invention to foliage, stems, and/or fruit of living plants range from 0.05 to 20 kilograms of active ingredient per hectare. More preferred rates are in the range of 0.1 to 10 kilos per hectare. The most preferred rates are in the range of 0.2 to 5 kilograms per hectare. The optimum amount within this range depends upon a number of variables which are well known to those skilled in the art of plant protection. The variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries, emulsions, or solutions.

The compositions of the invention can contain, in addition to the active ingredient of this invention, conventional insecticides, miticides, bactericides, nematicides, fungicides, or other agricultural chemicals such as fruit set agents, fruit thinning compounds, fertilizer ingredients and the like. Combinations with other fungicides, particularly maneb, captafol and chlorthalonil, are often preferred. The additional agricultural chemicals are employed in mixtures or combinations in amounts ranging from one to twenty times that of the compound or compounds of this invention. The proper choice of the additive chemical and amounts is readily made by one skilled in the art of protecting plants from pest depredations. The following are illustrative of the agricultural chemicals that may be included in compositions of the compounds of this invention or, additionally, that may be added to sprays containing one or more of the active compounds of this invention:

bis(dimethylthiocarbamoyl)disulfide or tetramethylthiuram disulfide (thiram);
metal salts of ethylenebisdithiocarbamic acid or propylenebisdithiocarbamic acids, e.g., manganese, zinc, iron and sodium salts (maneb or zineb);
n-dodecylguanidine acetate (dodine);
N-(trichloromethylthio)phthalimide (folpet);
N-[(trichloromethyl)thio]-4-cyclohexene-1,2-dicarboximide (captan);
cis-N-[(1,1,2,2-tetrachloroethyl)thio]-4-cyclohexene-1,2-dicarboximide (captafol);
2,4-dichloro-6-(o-chloroanilino)-s-triazine ("Dyrene");
3,3'-ethylenebis(tetrahydro-4,6-dimethyl-2H-1,3,5-thiadiazine-2-thione) (milneb);
triphenyltin hydroxide (fentin hydroxide);
triphenyltin acetate (fentin acetate);
N'-dichlorofluoromethylthio-N,N-dimethyl-N'-phenylsulfamide (dichlofluanid);
tetrachloroisophthalonitrile (chlorthalonil);
tribasic copper sulfate;
fixed copper;
sulfur;
methyl 1-(butylcarbamoyl)-2-benzimidazolecarbamate (benomyl);
methyl 2-benzimidazolecarbamate;
1,2-bis(3-methoxycarbonyl-2-thioureido)benzene (methyl thiophanate).

The agricultural chemicals listed above are merely exemplary of the compounds which can be mixed with the active compounds of this invention and are not intended to any way limit the invention.

The use of pesticides in combination with a compound within the scope of this invention sometimes appears to greatly enhance the activity of the active compound of the invention. An unexpected degree of activity is sometimes seen when another pesticide is used along with the methods of this invention.

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) and about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing. Likewise, oils and humectants may be incorporated or tank mixed.

Typical solid diluents are described in Watkins, et al., "Handbook of Insecticide Dust Diluents and Carriers," 2nd Edn., Dorland Books, Caldwell, N.J. The more absorptive diluents are preferred for wettable powders and the denser ones for dusts. Typical liquid diluents and solvents are described in Marsden, "Solvents Guide," 2nd Edn., Interscience, New York, 1950. Solubility under 0.1% is preferred for suspension concentrates; solution concentrates are preferably stable against phase separation at 0°C. "McCutcheon's Detergents and Emulsifiers Annual," Allured Publ. Corp., Ridgewood, New Jersey, as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, control pH, etc.

Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," Chemical Engineering, Dec. 4, 1967, pp. 145 ff. and "Perry's Chemical Engineer's Handbook," 4th Edn., McGraw-Hill, N.Y., 1963, pp. 8–59 ff.

For further information regarding the art of formulation, see, for example:

J. B. Buchanan, U.S. Patent 3,576,834, April 27, 1971, Col. 5, Line 36 through Col. 7, Line 70, and Ex. 1–4, 17, 106, 123–140.

R. R. Shaffer, U.S. Patent 3,560,616, Feb. 2, 1971, Col. 3, Line 48 through Col. 7, Line 26, and Examples 3–9, 11–18.

E. Somers, "Formulation," Chapter 6 in Torgeson, "Fungicides," Vol. I, Academic Press, New York, 1967.

The following examples further illustrate the invention. All parts and percentages are by weight.

EXAMPLE 1

Preparation of 2-Cyano-N-cyclopropylcarbamoyl-2-methoxyiminoacetamide

Cyclopropylurea (Chem. Abstr. 69, 2319), 57 grams, cyanoacetic acid, 54 grams, and 115 ml. of acetic anhydride were stirred and heated on a steam bath. When the temperature of the mixture reached 85°, heat of reaction evolved and external cooling was applied to keep the temperature under control. After stirring for 1 hour on the steam bath, the mixture was cooled and the cyanoalkylurea was recovered by filtration, washing with ether and drying. Yield 66 grams, mp 170°–2°.

Sixty-three and one-half grams of the above urea was suspended in 250 ml. of acetic acid. The suspension was cooled to 10° and a solution of 46 g of sodium nitrite in 68 ml. of $H_2O$ was added dropwise with stirring. After stirring overnight, 32 ml. of concentrated hydrochloric acid was added dropwise to the thick suspension with stirring and cooling in ice. The 2-cyano-N-cyclopropylcarbamoyl-2-hydroxyiminoacetamide was filtered, washed with water and ether, and dried. Yield 64 g, mp 210°–2°.

The above oxime, 3.9 grams, was dissolved in 30 ml. of acetone, and 1.6 grams of powdered anhydrous potassium carbonate and 2.2 ml. dimethyl sulfate were added. The mixture was stirred and refluxed for 2 hours. It was then cooled in ice, and the product was precipitated by adding ice water. After filtering, washing with water and ether, and drying, the product weighed 3.8 grams. Recrystallization from absolute alcohol afforded 3.2 grams of 2-cyano-N-cyclopropylcarbamoyl-2-methoxyiminoacetamide, mp 181.5°–182.5°.

EXAMPLE 2

Preparation of 2-Cyano-N-cyclopropylmethylcarbamoyl-2-methoxyiminoacetamide

Fifty grams of cyclopropylmethylamine HCl (Columbia Organic Chemicals Co.) was dissolved in 160 ml. water. Potassium cyanate (57 g) was added in portions with stirring. The solution was then heated for 3 hours on a steam bath. The mixture was vacuum concentrated to dryness, and the solid residue was extracted exhaustively with boiling absolute ethanol. The combined extracts were vacuum concentrated, and successive crops of the desired cyclopropylmethylurea isolated, mp 116°–8°. Yield 27.5 grams.

Twenty-six grams of the above urea was stirred and heated on the steam bath with 21.4 g of cyanoacetic acid and 46 ml. of acetic anhydride for 1 hour. There was some heat evolution when the temperature of the mixture reached 85°. The mixture was then cooled, filtered, washed with ether and dried. The yield was 26 grams, mp 156°–8°.

The above cyanoacetylurea, 24 grams, was slurried in 100 ml. acetic acid. The slurry was stirred at about 15°, and a solution of 16.5 grams $NaNO_2$ in 24 ml. of $H_2O$ was added dropwise. After stirring overnight at room temperature, the thick slurry was treated dropwise with 11 ml. of concentrated hydrochloric acid while cooling. The desired hydroxyimino compound was collected on a filter, washed with ice water and ether and dried. The yield was 25 grams of 2-cyano-N-cyclopropylmethylcarbamoyl-2-hydroxyiminoacetamide melting at 200°–2°.

The above oxime, 3.1 grams, was dissolved in 25 ml. of acetone. Powdered, anhydrous $K_2CO_3$ (1.2 g) and dimethyl sulfate (1.7 ml.) were added, and the mixture was stirred and refluxed for 2 hours. The product was precipitated by the addition of ice water to the cooled reaction mixture. After filtering, washing with ice water and ether, and drying, the product weighed 2.4 grams. After recrystallization from absolute ethanol, the product 2-cyano-N-cyclopropylmethylcarbamoyl-2-methoxyiminoacetamide weighed 2.2 grams and melted at 148.5°–149°.

The following compounds can be made in a similar manner:

2-cyano-N-cyclopropylcarbamoyl-2-ethoxyiminoacetamide, mp 136.5°–138° and 2-cyano-N-cyclopropylmethylcarbamoyl-2-ethoxyiminoacetamide.

EXAMPLE 3

A wettable powder formulation can be made and applied as follows:

| | Percent |
|---|---|
| 2-cyano-N-cyclopropylcarbamoyl-2-methoxyiminoacetamide | 50 |
| sodium alkylnaphthalenesulfonate | 2 |
| low-viscosity methylcellulose | 2 |
| diatomaceous earth | 46 |

The ingredients are blended, coarsely hammer-milled and then air-milled to produce particles of active essentially all below 20 microns in diameter. The product is reblended before packaging.

All compounds of the invention may be formulated similarly.

This formulation is dispersed in water in an amount sufficient to provide a concentration of 400 ppm of the active compound of this invention. The dispersion is sprayed to the point of run-off on potted tomato plants and allowed to dry. Both treated and untreated plants are inoculated with a spore suspension of *Phytophthora infestans* and incubated for a day in a saturated humidity chamber. After five days of additional incubation in the greenhouse, all of the untreated tomatoes are dead because of late blight disease. The plants treated with the 400 ppm concentration are healthy with little sign of disease. 2-Cyano-N-cyclopropylmethylcarbamoyl-2-methoxyiminoacetamide can be substituted for 2-cyano-N-cyclopropylcarbamoyl-2-methoxyiminoacetamide with like results.

EXAMPLE 4

The formulation of Example 3 can be mixed in a spray tank with the fungicide benomyl. This formulation can be diluted to a concentration of 500 ppm of the active ingredient. The benomyl in the mixture should be at a concentration of 100 ppm. Sprays can be applied to the point of run-off each week during the growing season to a cucumber field subject to infection by the downy mildew fungus (*Pseudoperonospora cubensis*), the powdery mildew fungus (*Erysiphe chichoracearum*), and the gummy stem blight fungus (*Mycosphaerella citrullina*). The plants which are sprayed with this mixture will be healthy and bear a normal crop whereas the unsprayed plants will be damaged by one or more of the fungi listed.

EXAMPLE 5

Potted greenhouse grown tomato plants are inoculated by spraying them with a spore suspension of *P. infestans*. They are incubated in a saturated humidity chamber at 20°C for 20 hours. The infected tomato plants are removed from the incubation chamber long enough to spray them with various disease control agents. The compounds listed below are dispersed at a concentration of 400 ppm of the active ingredient. Three infected plants are sprayed with enough dispersion to have run-off of dry plants. After treatment, the plants are placed in a greenhouse for an additional five days incubation. The untreated plants are dead because of the late blight disease. The treated plants are rated for percent of foliage which is healthy (percent disease control). The curative action of the compounds of this invention is demonstrated in the following table:

| Compound | Percent Disease Control |
|---|---|
| 2-cyano-N-cyclopropylcarbamoyl-2-methoxyiminoacetamide | 100 |
| 2-cyano-N-cyclopropylmethylcarbamoyl-2-methoxyiminoacetamide | 100 |
| water treatment check | 0 |

EXAMPLE 6

A wettable powder formulation can be prepared as follows:

| | Percent |
|---|---|
| 2-cyano-N-cyclopropylcarbamoyl-2-ethoxyiminoacetamide | 80 |
| sodium alkylnaphthalenesulfonate | 2 |
| sodium ligninsulfonate | 2 |
| synthetic amorphous silica | 3 |
| kaolinite | 13 |

The ingredients can be thoroughly blended, passed through a hammer-mill to produce an average particle size under 40 microns, reblended and sifted through a U.S.S. No. 50 sieve (0.3 mm openings) before packaging.

This formulation can be applied as follows: Select a potato field in which there is a uniform but light infection of the late blight disease and in which the older foliage of each plant supports one or two sporulating *Phytophthora infestans* lesions. The plant damage at this point should be slight, but the potential for disease spread will be high. Designate plots as five rows wide and 20 meters long. Assign treatments to various plots randomly through the field leaving much of the field untreated as buffers between treated plots. Select a series of treatments for application immediately following weather conditions conducive to disease spread. Include among those treatments the formulation of this example dispersed in water at a concentration of 300 ppm of active ingredient. Other treatments should include a representation of commercially available fungicides such as maneb, captafol, and chlorothalonil, applied at their recommended use rate. In addition to these single compound applications, apply combinations of the formulation of this example with each of the commercial fungicides at rates of ½ of that used alone. Make spray applications immediately after an overnight rain which had the potential of spreading the disease. After 1–2 weeks, the untreated foliage in this field should be completely killed by the late blight disease. Those plots receiving treatments of commercial fungicides will be severely diseased and about 80% defoliated. Those plots receiving the formulation of this example will be protected from the late blight disease and only slightly defoliated. Those plots receiving the combination of the formulation of this invention plus a commercial fungicide will be healthy and free of active disease. The other compounds of this invention may be substituted with like results.

EXAMPLE 7

A wettable powder can be prepared as follows:

| | Percent |
|---|---|
| 2-cyano-N-cyclopropylcarbamoyl-2-ethoxyiminoacetamide | 80 |
| sodium dioctyl sulfosuccinate | 1 |
| sodium ligninsulfonate | 2 |
| attapulgite | 17 |

The ingredients can be blended and passed through a hammer mill fitted with a coarse screen. After reblending, the product is hammer milled and packaged.

Inoculate greenhouse grown grape plants by spraying with a spore suspension of *Plasmopara viticola*, downy mildew. After 20 hours incubation in a 20°C saturated humidity chamber, spray six of the plants to run-off with the above formulation dispersed in water to give 100 ppm active ingredient. Treat similar plants with maneb at 2000 ppm active. After two weeks incubation in a greenhouse, the untreated plants and plants treated with maneb will be severely infected with downy mildew (about 90 percent of the susceptible leaves will be defoliated). Plants treated with the above formulation will be free of disease, demonstrating the curative effect.

EXAMPLE 8

| Wettable Powder | |
|---|---|
| 2-cyano-N-cyclopropylmethylcarbamoyl-2-methoxyiminoacetamide | 40% |
| dioctyl sodium sulfosuccinate | 1.5% |
| sodium ligninsulfonate | 3% |
| low-viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 9

| Wettable Powder | |
|---|---|
| 2-cyano-N-cyclopropylcarbamoyl-2-methoxyiminoacetamide | 80% |
| sodium alkylnaphthalenesulfonate | 2% |
| sodium ligninsulfonate | 2% |
| synthetic amorphous silica | 3% |
| kaolinite | 13% |

The ingredients are blended, passed through a hammer mill to produce a product at least 95% smaller than 44 μ (U.S.S. No. 325 wet screen).

EXAMPLE 10

| Oil Suspension | |
|---|---|
| 2-cyano-N-cyclopropylcarbamoyl-2-methoxyiminoacetamide | 25% |
| polyoxyethylene sorbitol hexaoleate | 5% |
| Oil Suspension | |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

| Dust | |
|---|---|
| 2-cyano-N-cyclopropylmethylcarbonyl-2-methoxyiminoacetamide | 10% |
| attapulgite | 10% |
| pyrophyllite | 80% |

The active ingredient is blended with attapulgite and then passed through a hammer mill to produce particles substantially all below 200 microns. The ground concentrate is then blended with powdered pyrophyllite until homogeneous.

I claim:
1. A compound of the formula

$$R-NH-\overset{O}{\underset{}{C}}-NH-\overset{O}{\underset{}{C}}-\underset{N-O-R_1}{C}-CN$$

wherein R is cyclopropyl or cyclopropylmethyl and $R_1$ is alkyl of 1 or 2 carbon atoms.

2. A compound of claim 1 wherein $R_1$ is methyl.

3. A composition useful for inhibiting fungus disease in plants caused by Phycomycetes consisting essentially of an amount of a compound of claim 1 sufficient to inhibit the fungus disease and at least one member selected from the group consisting of surfactants and diluents.

4. A composition of claim 3 wherein $R_1$ is methyl.

5. A method of protecting plants from fungus disease caused by Phycomycetes consisting essentially of applying to the plants an amount of a compound of claim 1 sufficient to inhibit the fungus disease.

6. A method of claim 5 wherein $R_1$ is methyl.

* * * * *